United States Patent [19]
Selker et al.

[11] Patent Number: 5,724,983
[45] Date of Patent: *Mar. 10, 1998

[54] CONTINUOUS MONITORING USING A PREDICTIVE INSTRUMENT

[75] Inventors: Harry P. Selker, Wellesley; John L. Griffith, Natick, both of Mass.

[73] Assignee: New England Center Hospitals, Inc., Boston, Mass.

[*] Notice: The term of this patent shall not extend beyond the expiration date of Pat. No. 5,501,229.

[21] Appl. No.: 621,246

[22] Filed: Mar. 25, 1996

Related U.S. Application Data

[63] Continuation-in-part of Ser. No. 283,951, Aug. 1, 1994, Pat. No. 5,501,229.
[51] Int. Cl.⁶ ........................................ A61B 5/04
[52] U.S. Cl. ........................................ 128/696
[58] Field of Search ........................ 128/696, 700, 128/702; 364/413.06, 113.03

[56] References Cited

U.S. PATENT DOCUMENTS

| | | | |
|---|---|---|---|
| 3,608,545 | 9/1971 | Novak et al. | 128/2.06 |
| 3,937,004 | 2/1976 | Natori et al. | 58/152 B |
| 4,181,135 | 1/1980 | Andresen et al. | 128/703 |
| 4,230,125 | 10/1980 | Schneider | 128/670 |
| 4,315,309 | 2/1982 | Coli | 364/200 |
| 4,347,851 | 9/1982 | Jundanian | 128/668 |
| 4,404,974 | 9/1983 | Titus | 128/670 |
| 4,422,081 | 12/1983 | Woods | 346/33 ME |
| 4,457,315 | 7/1984 | Bennish | 128/704 |
| 4,610,254 | 9/1986 | Morgan et al. | 128/419 D |
| 4,664,125 | 5/1987 | Pinto | 128/672 |
| 4,679,144 | 7/1987 | Cox et al. | 364/417 |

(List continued on next page.)

FOREIGN PATENT DOCUMENTS 5 99407  11/1987  Australia ............... A61B 5/04

OTHER PUBLICATIONS

Cohen et al., "Automated Electroencephalograpic Analysis As A Prognositc Indicator In Stroke", Medical and Biological Engineering & Computing 431–437 (Jul. 1977).

Gillum et al., "International Diagnostic Criteria For Acute Myocardial Infarction And Acute Stroke", Progress In Cardiology, American Heart Journal 150–158 (Jul. 1984).

Harvey et al., "1985 Yearbook of Cardiology", pp. 170–173.

Krucoff et al., "Noninvasive Detection Of Coronary Artery Patency Using Continous ST–Segment Monitoring", American Journal of Cardiology 1986; 57:916–922.

Krucoff et al., "The Portable Programmable Microprocessor–Driven Real–Time 12–Lead Electrocardiographic Monitor: A Preliminary Report Of A New Device For The Noninvasive Detection Of Successful Reperfusion or Silent Coronary Reocclusion", American Journal of Cardiology 1990; 65:143–148.

Krucoff et al., "Heuristic And Logistic Principles Of ST–Segment Interpretation In The Time Domain", Journal of Electrocardiology vol. 23 supplement (pp.6–10).

Long et al., "A Comparison Of Logistic Regression To Decision–Tree Induction In A Medical Domain", Computers And Biomedical Research 26, 74–97 (1993).

(List continued on next page.)

Primary Examiner—Scott Getzow
Attorney, Agent, or Firm—Fish & Richardson P.C.

[57] ABSTRACT

A method for continuously monitoring the medical condition of a patient, the method including the steps of continuously monitoring one or more clinical features of the patient; periodically computing a probability of a medical outcome or diagnosis based upon the continuously monitored one or more clinical features; from the periodically computed probability of a medical outcome or diagnosis, computing a change-of-condition measure; periodically comparing the change-in-condition measure to a threshold value; and if any computed change-in-condition measure exceeds the threshold value, generating an alarm notification.

5 Claims, 3 Drawing Sheets

U.S. PATENT DOCUMENTS

| | | | |
|---|---|---|---|
| 4,680,708 | 7/1987 | Ambos et al. | 364/417 |
| 4,754,762 | 7/1988 | Stuchl | 128/696 |
| 4,893,270 | 1/1990 | Beck et al. | 364/900 |
| 4,945,477 | 7/1990 | Edwards | 364/413.06 |
| 4,957,115 | 9/1990 | Selker | 128/696 |
| 4,974,598 | 12/1990 | John | 128/696 |
| 4,998,535 | 3/1991 | Selker et al. | 128/696 |
| 5,046,499 | 9/1991 | Berger | 128/654 |
| 5,054,493 | 10/1991 | Cohn et al. | 128/672 |
| 5,276,612 | 1/1994 | Selker . | |

OTHER PUBLICATIONS

Pozen et al., "A Predictive Instrument To Improve Coronary–Care–Unit Admission Practices In Acute Ischemic Heart Disease", New England Journal of Medicine; 310:1273–1278 (May 1984).

Cardiology Update, Review For Physicians, 1986 Edition by Elliot Rappaport, "Thrombolysis In Accute Myocardial Infarction", by Sherman et al., pp. 117–135.

| Variable | Coefficients ($b_i$) | | Values $(x_i)$[a] |
|---|---|---|---|
| CONSTANT ($b_0$) | −3.933 | | |
| CPAIN | 1.231 | chest of left arm pain/pressure present | 1 |
| | | not present | 0 |
| SX1CPAIN | 0.882 | chest or left arm pain chief complaint | 1 |
| | | otherwise | 0 |
| MALESEX | 0.712 | male | 1 |
| | | female | 0 |
| AGE 40 | −1.441 | patient age 40 yrs or less | 1 |
| | | otherwise | 0 |
| AGE50 | 0.667 | patient age greater than 50 yrs. | 1 |
| | | otherwise | 0 |
| SEXAGE50 | −0.426 | male patient age greater than 50 yrs | 1 |
| | | otherwise | 0 |
| QWAVE | 0.616 | ECG Q waves present | 1 |
| | | otherwise | 0 |
| STEL | 1.314 | ECG S-T segment elevated 2 mm or more | 2 |
| | | ECG S-T segment elevated 1-2 mm | 1 |
| | | otherwise | 0 |
| STDEP | 0.993 | ECG S-T segment depressed 2 mm or more | 2 |
| | | ECG S-T segment depressed 1-2 mm | 1 |
| | | ECG S-T segment depressed 0.5-1.0 mm | 0.5 |
| | | otherwise | 0 |
| TWEL | 1.095 | ECG T-waves elevated ("hyperacute) | 1 |
| | | otherwise | 0 |
| TWINV | 1.127 | ECG T-waves inverted 5 mm or more | 2 |
| | | ECG T-waves inverted 1-5 mm | 1 |
| | | ECG T-waves flat | 0.5 |
| | | otherwise | 0 |
| TWISTDEP | −0.314 | <u>Both</u> STDEP and TWINV not 0 | 1 |
| | | otherwise | 0 |

FIG. 2

CONTINUOUS MONITORING USING A PREDICTIVE INSTRUMENT

BACKGROUND OF THE INVENTION

This is a continuation-in-part of U.S. patent application Ser. No. 08/283,951, by Harry P. Selker et al., filed Aug. 1, 1994, and incorporated herein by reference now U.S. Pat. No. 5,501,229.

The invention relates to predictive instruments for computing a patient's probability of a serious medical condition.

A number of instruments have been developed that enable the physician to compute probabilities of life threatening cardiac conditions for patients. Some of these instruments are described in the following references, all of which are incorporated herein be reference.

A hand-held predictive instrument is described by Michael W. Pozen et al. in "A Predictive Instrument to Improve Coronary-Care-Unit Admission Practices in Acute Ischemic Heart Disease" The New England Journal of Medicine, Vol 310 pp. 1273–1278, May 17, 1984. With the handheld calculator-based instrument, a physician can compute a patient's probability of having acute cardiac ischemia based upon physician-entered values for a set of clinical variables. An automatic, computerized version of this instrument which utilizes output from a electrocardiograph and a waveform analyzer is described by H. P. Selker et al. in "A Time-Insensitive Predictive Instrument for Acute Myocardial Infarction Mortality", Med. Care 1991; 29:1196–1211.

A predictive instrument for determining the probability of acute hospital mortality of a cardiac patient is described in U.S. Pat. No. 4,957,115 to Dr. Harry P. Selker, and incorporated herein by reference. The probability of acute hospital mortality is commonly understood to mean the probability of dying from a current acute condition, generally during the specific initial hospitalization for the problem. It is also referred to as the probability of imminent death for the patient. That is, it is a short term, as opposed to a long term, probability of mortality which does not necessarily have a precisely defined period of time associated with it.

A predictive instrument for evaluating whether to use thrombolytic therapy to treat a patient with a heart condition is described in U.S. Pat. No. 4,998,535 to Dr. Selker et al., and incorporated herein by reference. The predictive instrument computes a first probability of acute hospital mortality for the patient assuming that thrombolytic therapy is not administered and it computes a second probability of acute hospital mortality for the patient assuming that thrombolytic therapy is administered. The difference in the computed probabilities may assist the physician in deciding whether it would be advantageous to administer the thrombolytic therapy to the patient.

The above-mentioned predictive instruments use logistic regression equations to model the probability that the patient has a serious cardiac condition (e.g. the probability of acute cardiac ischemia or the probability of imminent death from a cardiac condition).

SUMMARY OF THE INVENTION

In general, in one aspect, the invention is an apparatus for continuously monitoring the medical condition of a patient. The apparatus includes a medical instrument which during use is connected to the patient to monitor one or more clinical features of the patient; a predictive instrument receiving output from the medical instrument and programmed to complete a monitoring cycle in which it uses the output from the medical instrument to compute a probability of a medical outcome or diagnosis based on the monitored clinical features; a control module causing the predictive instrument to periodically repeat the monitoring cycle; and a detector module receiving the computed probabilities resulting from the repeated monitoring cycles and computing therefrom a change-of-condition measure. The detector module is further configured to compare for each monitoring cycle the computed change-of-condition measure for that monitoring cycle to a threshold value and if in excess of the threshold value to generate an alarm notification.

In general, in another aspect, the invention is a method for continuously monitoring the medical condition of a patient. The method includes the steps of continuously monitoring one or more clinical features of the patient; periodically computing a probability of a medical outcome or diagnosis based upon the continuously monitored one or more clinical features; from the periodically computed probability of a medical outcome or diagnosis, computing a change-of-condition measure which represents a change in a computed probability for a current monitoring cycle relative to a previous monitoring cycle; periodically comparing the change-in-condition measure to a threshold value; and if any computed change-in-condition measure exceeds the threshold value, generating an alarm notification.

Other advantages and features will become apparent from the following description of the preferred embodiment and from the claims.

DESCRIPTION OF THE PREFERRED EMBODIMENTS

Figure 1:
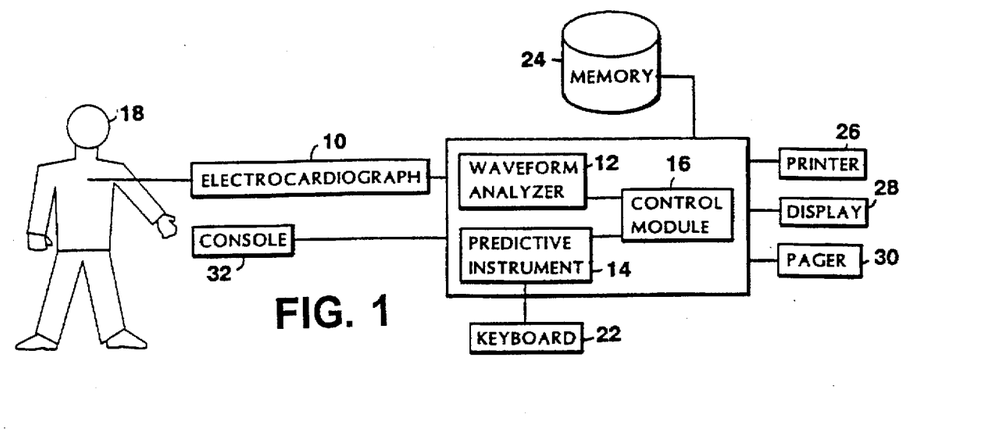
FIG. 1 is a block diagram of a patient monitoring system constructed in accordance with the invention.

Referring to FIG. 1, a cardiac patient monitoring system constructed in accordance with the invention includes a 12-lead electrocardiograph 10, a waveform analyzer 12, a predictive instrument 14, and a control module 16. Electrocardiograph 10 is connected to a patient 18 and produces a set of ECG waveforms for the patient. Waveform analyzer 12 is programmed to analyze the ECG waveforms and recognize the presence of certain characteristics that are particularly indicative of the cardiac condition of the patient, e.g. the presence and elevation or depression of S-T segments, the presence Q waves, and the presence of elevated, depressed or inverted T-waves. The particular characteristics which the waveform analyzer is programmed to recognize depend upon the function that is performed by the predictive instrument which in turn determines the set of clinical variables that are required to perform that function. Predictive instrument 14 uses the output of waveform analyzer 12 in conjunction with other clinical information about the patient that has been entered by a physician through a keyboard 22 and computes a probability that the patient has a life-threatening cardiac condition. Control module 16 controls the operation of the other components in the system, detects a change in the computed probability patient's condition, and takes appropriate actions when the detected change exceeds certain thresholds, e.g. storing the measurements in a digital memory 24 (e.g. RAM or disk storage), printing a report out on a printer 26 attached to the system, displaying the report on a video screen 28, or notifying medical support staff when the patient's condition has deteriorated significantly (e.g. by using a pager 30 to send a page to the physician).

Electrocardiograph 10 and waveform analyzer 12 are commercially available as a single unit. For example, Hewlett Packard makes the HP Pagewriter XLi which is a mobile unit that can be moved from one patient to the next. The Pagewriter XLi includes a built-in 80386-based computer that can be programmed to perform the appropriate waveform analysis. For example, it can be programmed to recognize and quantify the presence of key features within the ECG waveform. It can also be programmed to identify the location of a myocardial infarction (MI) based on the characteristics of the set of signals produced by the twelve monitoring leads. Besides performing the wave analysis functions, the computer within the unit can also be programmed to perform the functions of other components or modules within the system, e.g. the computations of the predictive instrument and the functions of the control module.

In the described embodiment, predictive instrument 14 is an ACI-TIPI (Acute Cardiac Ischemia Time-Insensitive Predictive Instrument) which uses a logistic regression-based equation for computing the probability that the patient is experiencing acute cardiac ischemia. The logistic regression equation is of the form:

$$P = 100 \left[ 1 - \frac{1}{1 + e^{b_0 + \Sigma b_i x_i}} \right]$$

where P is the probability of acute cardiac ischemia, $b_0$ is a constant, and the $b_i$'s are coefficients of the variables $x_i$ which are included in the model.

Figure 2:
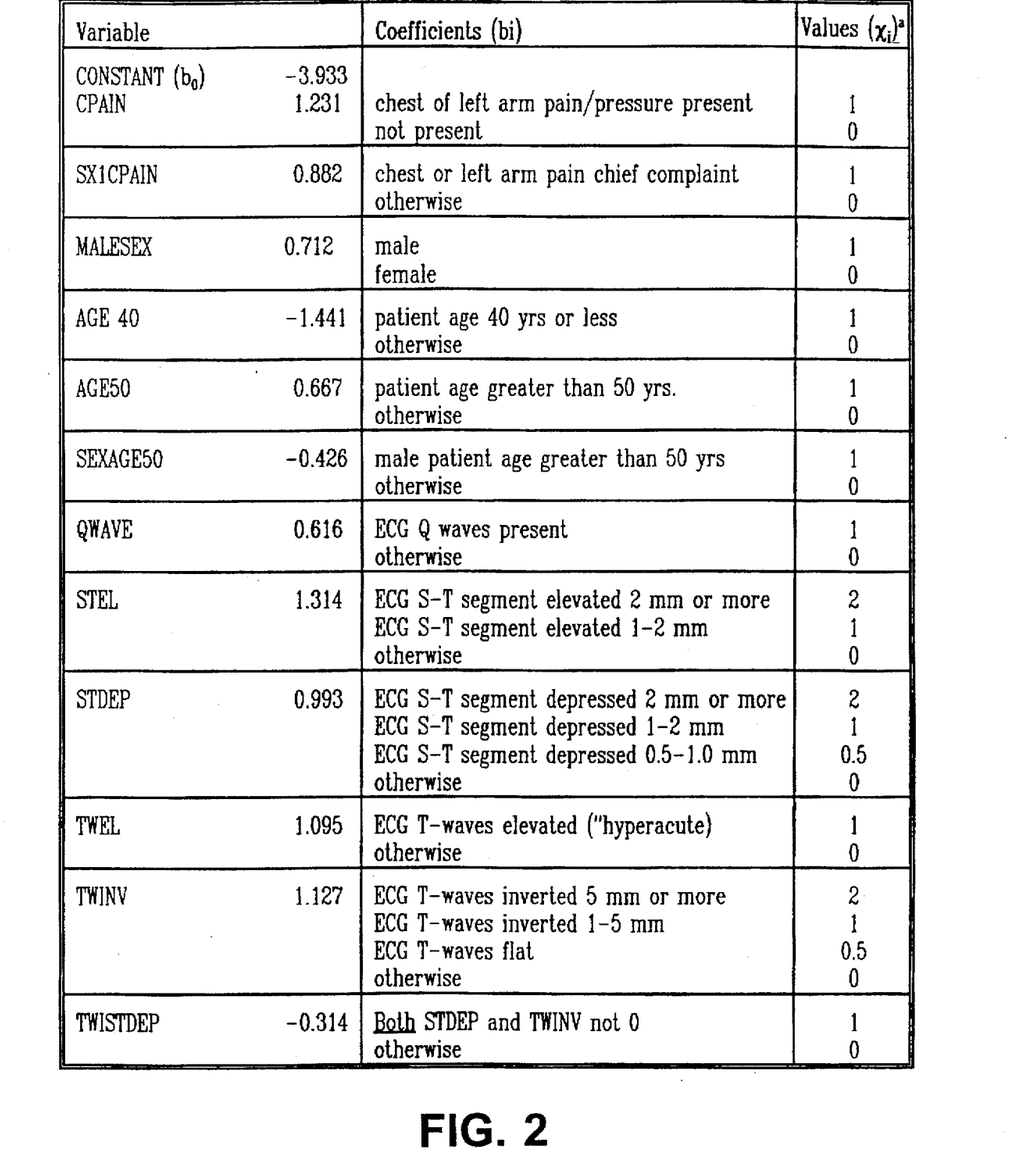
FIG. 2 presents the coefficients and variables of an example of a logistic regression equation used to predict a particular cardiac outcome, e.g. the probability of acute cardiac ischemia.

The variables which are used in this equation are shown in FIG. 2 along with the values of the coefficients and the values which the $x_i$'s can take for the different variables. Note that only the largest value for x is used per variable. Also ECG findings must be present in at least two leads, and S-T segment and T wave changes are "normal" if secondary to right or left complete bundle branch blocks, left ventricular hypertrophy, or a paced QRS. Only one type of abnormality is coded each for S-T segment and for T wave per patient (exclusive of TWISTDEP), use with elevation taking priority. Deviations are expressed in mm using the standard ECG scale of 1 mm=0.1 mV.

Figures 3, 4:
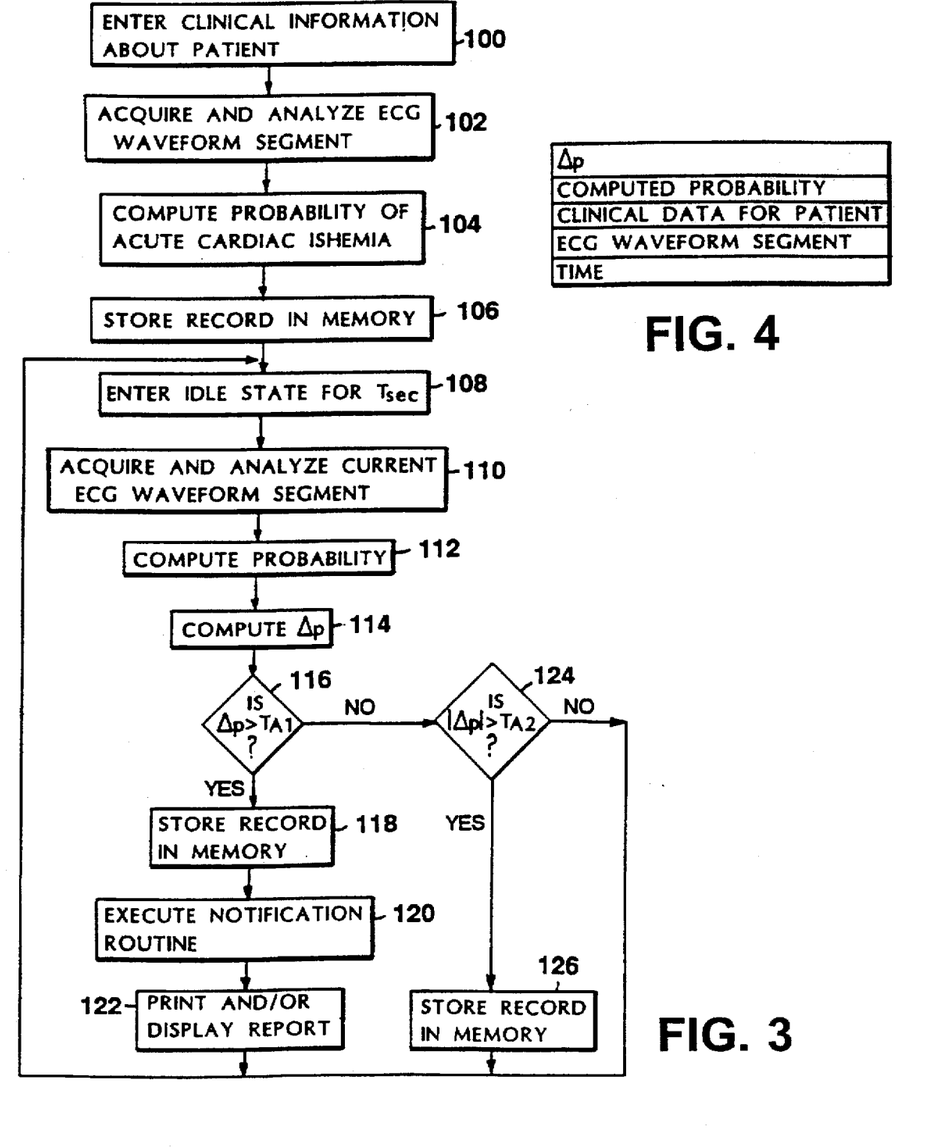
FIG. 3 is a flow chart showing the operation of the system shown in FIG. 1.
FIG. 4 shows the record data structure which the control module stores in memory.

The system is programmed to operate in the manner shown in FIG. 3. When the patient is first connected to the system, the physician enters the relevant clinical information about the patient (step 100). For example, if the predictive instrument is programmed to compute the probability of acute cardiac ischemia in accordance with the above model, the physician enters the following information about the patient: (1) name; (2) age; (3) sex; (4) whether the patient is experiencing chest or left arm pain; and (5) whether the patient's chief complaint is chest or left arm pain. After the physician has set up the system for a particular patient and connects the leads of the electrocardiograph to the patient, the physician causes the system to perform an initial ECG for the patient. In response, the waveform analyzer acquires and analyzes a current segment of the patient's ECG waveform (step 102). Typically, a 10–20 second segment of the patient's ECG is required by the waveform analyzer to perform its waveform analysis functions. The output of the waveform analyzer passes to the predictive instrument, which may, for example, be implemented by a computation routine within the computer. In the present embodiment, the output of the waveform analyzer reports whether: (1) any Q waves are present; (2) whether the S-T segment is elevated or depressed and by how much; (3) whether the T-waves are elevated inverted or flat; (4) if the T-waves are elevated, by how much; and (5) whether both the STDEP and TWINV leads are non-zero.

Using the output of the waveform analyzer and previously entered values for other clinical variables, the predictive instrument computes a probability that the patient has acute cardiac ischemia (step 104). The control module then stores a record of the computation in memory (step 106). Referring to FIG. 4, the record includes the computed probability along with the underlying clinical information, the ECG waveforms from which the probability was generated, and a time-stamp indicating when the measurement was performed.

Thereafter, the control module enters a monitoring mode in which it periodically executes a monitoring cycle. At the beginning of each monitoring cycle the system enters an idle state for a user-selectable period of time, $T_{sec}$ (step 108). At the end of the idle period, the control module causes the waveform analyzer to acquire and analyze a segment of the current ECG waveform and pass its results to the predictive instrument (step 110). The predictive instrument then computes an updated probability for the patient based on the patient's current ECG waveform (step 112). The control module computes $\Delta_p$ which is measure of the change (or delta) in the patient's condition since the last recorded monitoring cycle (step 114). In the described embodiment, $\Delta_p$ is equal to the proportional change in the computed probability $$\left( \text{i.e., } \Delta_p = \frac{P_{new} - P_{last}}{P_{last}} \right),$$

where $P_{last}$ equals the last recorded probability and $P_{new}$ equals the current computed probability.

The control module compares the computed change statistic $\Delta_p$ to a first threshold $T_{A1}$, which represents an alarm threshold or the threshold for clinical activity (step 116). That is, changes that are larger than $T_{A1}$ are considered to be significant enough to deserve the immediate attention of medical staff. If $\Delta_p$ exceeds $T_1$, the control module stores in memory a record containing the value of the newly computed probability, the value of $\Delta_p$, the underlying clinical information, the corresponding ECG waveform, and a time-stamp indicating when the measurement was performed (step 118). The control module also executes a notification routine which notifies medical staff of the patient's worsening condition (step 120). The notification may be in any one or more of many possible forms. For example, the notification routine might cause a page to be sent to the responsible physician, it might generate an audible alarm at the location of the mobile monitoring unit, it might send a message to the central nursing station which would appear on a central display monitor and also trigger an audible alarm at the nurse's station, or it might perform any combination of those or similar actions.

After the control module has executed the notification routine, it displays and/or prints a report of the computed probability, the underlying ECG waveforms and a history of the computed probabilities over a selected period of time prior to the most recent monitoring cycle (step 122). The control module then causes the system to enter the idle state for the preselected delay period or until the patient or medical staff enters new clinical information reflecting a change in the patient's condition.

In the event that $\Delta_p$ is not greater than $T_{A1}$, the control unit compares the absolute value of $\Delta_p$ to a lower threshold $T_{A2}$ (step 124). Threshold $T_{A2}$ defines a level below which the change in the patient's condition is considered to be not large enough to be clinically significant. If $\Delta_p$ exceeds $T_{A2}$, the control module stores a record of the measurement including the computed probability, $\Delta_p$, the underlying data, the ECG waveform, and a time-stamp indicating when the measurement was performed (step 126). This record then defines the reference from $\Delta_p$ is computed for the next computed probability.

Threshold $T_{A2}$ is set so that the system will generate a history of the patient's condition containing records of only the clinically meaningful events. Using the second threshold as a criteria for storing monitoring data greatly reduces the amount of information that is stored by the monitoring system. Thus, the limited system memory is not filled with clinically redundant information.

After a monitoring cycle is complete, the system returns to an idle state for the preselected period of time. Then, it begins a new monitoring cycle. The above-described sequence repeats until the user terminates it.

As alluded to above, it is possible to manually trigger a monitoring cycle by entering new values for relevant clinical variables. For example, if the patient begins to experience chest pain, he can enter this new information through a bedside console 32 (see FIG. 1), or alternatively, medical staff can enter it through another input device. Entering the changed clinical information causes the control unit to immediately initiate a new monitoring cycle immediately or, if it is currently in the middle of a monitoring cycle, to initiate a monitoring cycle immediately after it has completed the current monitoring cycle.

The system also has a manual mode of operation in which the probability is computed only when medical staff manually initiates a new monitoring cycle by, for example, pushing an appropriate button on the bedside control console. In all other respects, the monitoring cycle which is initiated is the same as the monitoring cycle described above.

It should be noted that the thresholds, $T_{A1}$ and $T_{A2}$, may be simple fixed value thresholds or they may be functions of some other variable, such as $P_{last}$. For example, with regard to $T_{A1}$ it may be desirable to have this value set higher for smaller values of $\Delta_p$ than for larger values of $\Delta_p$. In other words, a 25% increase from an initial probability of 5% would probably not be significant whereas a 25% increase from an initial probability of 40% would probably provide a basis for real concern.

In addition, the thresholds can be a function of previous computed changes. For example, two successive $\Delta_p$'s both indicating a worsening condition provide a greater basis for concern than does a sequence of $\Delta_p$'s that alternate between positive and negative values. In other words, the threshold could be set as a function of the direction (or sign) of computed change for previous monitoring cycles. If the previous computed value for $\Delta_p$ was positive (e.g. indicating a worsening condition), the threshold for the next computed value of $\Delta_p$ might be lower than it would be if the previous computed value for $\Delta_p$ was negative.

Also $\Delta_p$ can be defined in any of a number of alternative ways. For example, it can be a rate of change computed by the change from the last recorded clinically meaningful event divided by the time difference between the current measurement and the last recorded measurement. Alternatively, it can simply be an absolute change (i.e., $P_{new} - P_{last}$).

The logistic regression equation presented above is presented as merely illustrative of one way in which the cardiac condition and the probability can be modeled. There are a variety of statistical methods and algorithms that can be used for calculating the predicted probability of an adverse cardiac event or a life threatening cardiac condition. These include, for example, artificial feed-forward multilayer neural networks and classification trees. Although the procedures may differ among these various techniques, many of them may generally be expressed in terms of finding an optimal solution to the following general equation:

$$f^{-1}(\text{probability of event}) = \beta_0 + \sum_{i=1}^{K} \beta_i g_i(X_1, X_2, \ldots X_p),$$

where $f^{-1}$ and $g_i$ are general functions, the $X_n$'s (where $1 \leq n \leq p$) are the values of the independent input variables, and $\beta_0$ and $\beta_i$ (where $1 \leq i \leq K$) are model coefficients.

The standard logistic regression equation described earlier can be derived from the above equation. In addition an artificial network with a single hidden layer and an activation function "h" can be written as:

$$f^{-1}(\text{output}) = \beta_0 + \sum_{i=1}^{K} \left\{ \beta_i h \left( \sum_{j=1}^{p} \alpha_{ij} X_j \right) \right\}.$$

The automatic, periodic monitoring of the patient's condition with the predictive instrument provides information that assists the physician in more accurately evaluating the seriousness of the patient's condition and in obtaining early detection of changes in the patient's condition. The advantages are illustrated by the following actual histories of four patients, identified as Patient A, Patient B, Patient C, and Patient D.

Patient A presented at the ED (Emergency Department) with a potentially life-threatening cardiac rhythm. The first computed probability of acute cardiac ischemia (i.e., either unstable angina pectoris or acute myocardial infarction, as opposed to a rhythm disturbance) was relatively low, at 10%. In a subsequent ECG taken 23 minutes later, the cardiac rhythm had returned to normal, which would lead to a conclusion of no remaining cardiac problem. Indeed, a usual ECG monitor would have shown the patient as having a normal rhythm and an essentially normal ECG. However, the ECG contained a relatively minor ST elevation in the anterior leads which caused the computed probability of acute cardiac ischemia to rise to 16%, representing a 60% increase from the previous computed probability. An increase of that amount flagged the patient as having acute cardiac ischemia and still requiring acute medical attention.

An interesting aspect of this example is that both of the computed probabilities are below the level at which patients are commonly sent home, which in the facility in which this patient was treated, is about 18%. Thus, a computed probability of 16% by itself is difficult to interpret because the physician does not know whether that is a normal reading for that patient. Just being of a certain age and gender and having chest pains can often result in more than 16% probability with no abnormality in ECG.

To more fully appreciate the significance of a computed probability of 16%, it is useful to explore what the figure actually means. A 16% reading indicates that among a representative population of 100 patients, all of whom arrive at the ED with presenting conditions that produce a probability of 16%, on average 16 of the patients will have acute ischemia and 84 patients will not have acute ischemia. Within that population, however, the predictive instrument based upon a single computation is not able to distinguish between the group of patients who have acute ischemia and the group of patients who do not have acute ischemia. By using the predictive instrument in accordance with the above-described invention, the physician is able to discover further information which will assist the physician in determining to which group the patient actually belongs.

By monitoring the change in the patient's computed probability, the physician was able to gain further information which helped interpret the initial reading of 10%. That is, the instrument detected a substantial change in the computed probability in a direction that flagged the patient as being more likely to fall within that category of patients who have acute ischemia.

In the case of Patient B, he arrived at the ED with a chest pain as his chief complaint. His initial computed probability of acute cardiac ischemia was 25%. However, chest pain in a properly aged male, who does not have acute cardiac ischemia, can still produce a relatively high probability. In other words, one can obtain that same probability in a variety of different ways, not all of which are symptomatic of acute cardiac ischemia. Thus, even though the presenting probability of 25% is a relatively high number, by itself its meaning to the physician is still ambiguous. It simply indicates that the patient falls into a category of patients who have historically exhibited higher risk than the group of patients who have generated lower computed probabilities. From the physician's perspective the predictive instrument is indicating that the patient has a one-in-four chance of having acute cardiac ischemia but the instrument is also indicating that the patient has a three-in-four chance of not having acute cardiac ischemia.

In the case of Patient B, a second ECG approximately one hour later still appeared to be relatively normal and again produced a computed probability of acute cardiac ischemia of 25%. However, in a subsequent electrocardiogram taken about two hours after the initial ECG, there were very subtle changes of lateral T wave flattening that produced a computed probability of 37%, clearly flagging the patient as requiring clinical activity. Such subtle changes would not have been flagged except for the fact that the predictive instrument magnifies any changes of this type. Thus, because the predictive instrument when used in a continuous manner amplifies the seemingly most trivial of changes in the patient's condition, it can give the physician further valuable information which will help him or her to accurately evaluate the patient's condition and make the correct admission decision.

Patient C, a woman with known cardiac problems, came into the ED with general complaint about not feeling well. When the monitor was connected to her, the computed probability was 10%. Nevertheless, because of her history of known problems she was admitted to the ward. While she was in the ward, she began to experience chest pains which caused the computed probability to jump up to 50%, an increase of about 400%, clearly flagging her for immediate clinical action.

Patient D, a 64 year old woman, represents yet another example of the invention's ability to help medical staff distinguish among patient's who have acute cardiac ischemia and those who do not. The patient's initial ECG was benign and the computed probability indicates only a 4% likelihood of acute cardiac ischemia. She was admitted to the ward because she was known to have bad coronary disease. In a subsequent ECG taken about 22 hours later, suddenly the very same ECG, coupled with a new chief complaint of chest pain, resulted in a six-fold increase in the probability of acute cardiac ischemia (i.e., 24%). In this case, the actual ECG was unchanged and thus a normal ECG heart monitor would not have picked up the significance of the new information. Moreover, this patient's final number (i.e., 24%) was below average for patients in the ED and, in fact, was within the range of numbers for patients who are sent home. However, because the delta (i.e., change in computed probability) was substantial she was flagged as a patient requiring further clinical activity.

Other embodiments are within the following claims. Even though the monitoring of the probability of acute cardiac ischemia for changes was used as an example, this was not meant to limit the scope of the invention to only those systems which compute that particular probability. The invention also encompasses systems which periodically compute and monitor for changes any probability of a serious cardiac condition. In addition, the method by which the probability is not computed is not central to the invention. Any approach which attempts to model historical patient information to compute a probability of the patient having a serious cardiac condition based at least in part upon ECG information falls within the scope of this invention.

In addition, continuous monitoring using a predictive instrument has applicability to many other medical problems beyond the above-described cardiac related problems. The extension to circumstances that are not cardiac related is straightforward. For example, in the domain of pulmonary medicine, a patient in an intensive care unit could be under observation for potential respiratory failure. The classical approach is to use on-going single function monitors of indicators such as the patient's heart rate, respiratory rate, and perhaps under some circumstances, blood oxygen saturation. As with the cardiac situation, however, any single one of these parameters has limited utility because of its possible contamination by noise and because of its inherent inability to be a good proxy for the wide variety of clinical features and other factors that are really needed to provide an accurate estimate of the probability of the medical outcome in question. On the other hand, the mathematical model described herein (e.g., logistic regression) that takes into account the heart rate, blood pressure, respiratory rate, blood oxygen saturation level, and perhaps other clinical features, will give a far more accurate indication of and prediction of true respiratory failure. The other clinical features include for example the patient's age, symptoms (e.g. shortness of breath), and the patient's past medical history (e.g., history of smoking, history of prior respiratory failure, etc.). In other words, the mathematical model will give a more accurate and usable (e.g. noise-free) estimate of the patient's condition.

A further example in the pulmonary area may be useful. In the case of imminent respiratory failure, a small increase in respiratory rate and heart rate would likely be missed, or might be overwhelmed by noise, or even if detected might be viewed as insignificant. However, if measured in conjunction with other clinical features, including for example a small decrease in oxygen saturation, these observations when included in a logistic regression (or other mathematical model) will be multiplicative, and thus, give a substantial (accurate and specific) increase in the computed probability of respiratory failure. Thus, since the mathematical model takes multiple factors into account, as in the cardiac monitoring situation, it will provide an opportunity to early on detect a change in the computed probability value with sufficient fidelity in the real-time setting to support targeted clinical intervention.

Figure 5:
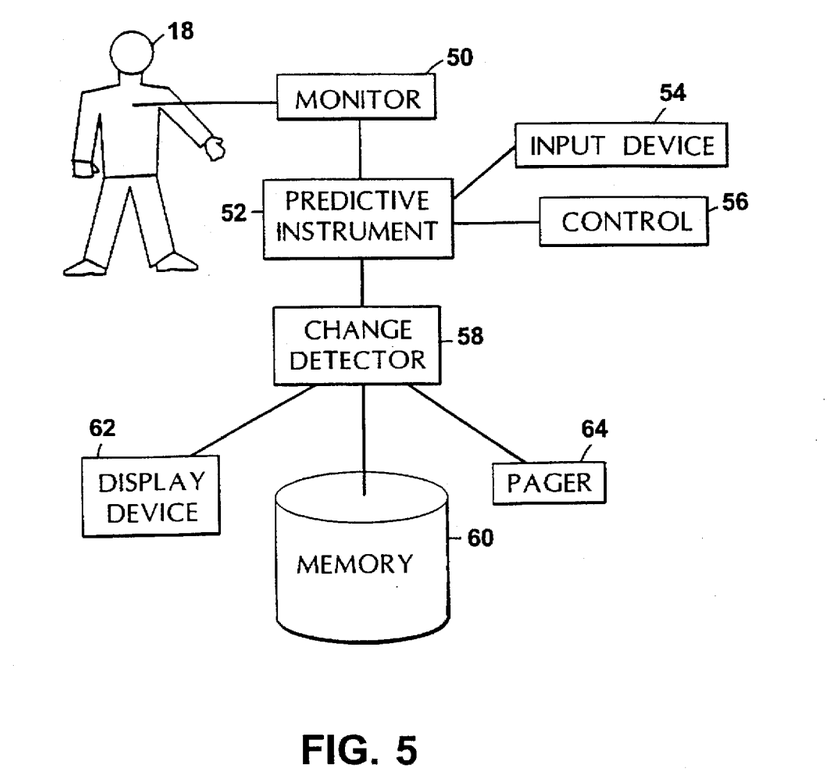
FIG. 5 is a block diagram of another general patient monitoring system constructed in accordance with the invention.

FIG. 5 shows a generalized continuous monitoring system which utilizes a device 50 for real-time monitoring of one or more clinical features of patient 18 and a predictive instrument 52 for computing a probability of a medical outcome or diagnosis, based in part on those monitored clinical features. The monitoring device 50 could be a single instrument, as it was in the case of the above-described cardiac monitor which used an electrocardiograph, or it could be a constellation of medical instruments, as will be the case in some of the examples systems described below.

Predictive instrument 52 uses the output of monitoring device 50 in conjunction with other clinical information about the patient that has been entered by a physician through an input device 54 (e.g. keyboard, network connection, database program, etc.) and computes a probability of a particular medical outcome or diagnosis for the patient. A control module 56 controls the operation of the other components in the system. For example, it causes the predictive instrument to periodically compute a new probability. A change detection module 58 receives the sequence of periodically computed probabilities from predictive instrument 52 and looks for a significant change in the computed probability from a previously received computed probability. If change detector module 58 detects a significant change in the patient's condition, as reflected by a change in the computed probability that exceeds a predetermined threshold, it takes appropriate actions, e.g. storing the measurements in a digital memory 60 (e.g. RAM or disk storage), generating and displaying a report through a display device 62 (e.g. printer or video display), or notifying medical support staff when the patient's condition has deteriorated significantly (e.g. by using a pager 30 to send a page to the physician).

The detector module, i.e., the portion of the system which detects when changes in the computed probabilities exceed a predetermined threshold, may be located locally to the monitoring device, the predictive instrument, and the control unit; or alternatively it can be located remotely from those devices. If it is located locally, it can be implemented within the same computer which computes the probabilities and which implements the functionality of the control unit. If it is located remotely from them, the computed probabilities are sent to the detector module by some appropriate method, e.g. modem, LAN network connection, transmitter, etc.

In the described embodiments, the probability of the medical diagnosis or medical outcome is computed using a logistic regression equation of the following general form:

$$P = 100 \left[ 1 - \frac{1}{1+e^z} \right]$$

where P is the probability of a particular medical outcome or diagnosis, and where z has the following general form:

$$z = b_O + \Sigma b_i x_i.$$

In this equation, $b_O$ is a constant, and the $b_i$'s are coefficients of the explanatory variables $x_i$ which are included in the model. The variables that are used in the model will of course depend upon the particular medical outcome or diagnosis which is being evaluated. Some examples are presented below along with variables that would be included in the model.

Standard, well known regression techniques may be employed to identify the most appropriate set of explanatory variables, namely, the $x_i$'s, and to determine the values of the coefficients of these variables. For a description of such techniques and examples of commercially available computer programs that implement them, see N. C. Cary in SUGI Supplement Library User's Guide, SAS Institute, p. 181–202, 1983, and L. Engelman, "PLR Stepwise Logistic Regression," BMDP Statistical Software, Chap. 14.5, pp. 330–334, BMDP publishers, Westwood, Calif. Of course, the precise set of explanatory variables that are identified and the predictive ability of the resulting logistic equation generally depends upon the quality of the underlying data that is used to develop the model. Such factors as the size and completeness of the database are often of significant importance. The selection of the relevant variables and the computation of the appropriate coefficients are well within the skill of an ordinary person skilled in the art.

As noted above in connection with the cardiac instrument, mathematical models other than the logistic regression equation can of course be employed. The invention is not limited to the use of a logistic regression equation to model the probability of a particular medical outcome or diagnosis.

The following are further examples of predictive instruments for noncardiac diagnoses or medical outcomes, along with their likely key clinical variables.

In the domain of vascular disorders, a predictive instrument for pulmonary embolus includes as key variables the same variables as listed above, as well as a modification of the symptoms regarding the suddenness of onset, and also ECG variables related to right heart strain (e.g. relating to QRS complex and ST/T wave changes).

In the domain of neurologic disorders, a predictive instrument for cerebral hemorrhage (i.e., hemorrhagic stroke) includes as key variables the patient's history of medications (e.g. anticoagulants, etc.), prior history of cardiac disorders that predispose to cerebral thrombosis (e.g. atrial fibrillation, valvular disease), and history of trauma to the head, as well as laboratory tests such as prothrombin time and partial thromboplastin time and platelet count, which are all measures of the clotting ability of the blood. They also include blood pressure, with emphasis on pulse pressure (i.e., a difference between the systolic and diastolic pressure).

In the domain of general surgery, a predictive instrument for intra-abdominal catastrophe (i.e., the need for emergency surgery) includes as key variables the presence of abdominal pain, the patient's physical findings by the physician of so-called peritoneal signs (rigidity of the abdomen, no bowel sounds, etc.), monitor data such as temperature, heart rate, blood pressure, and potentially x-ray findings that reveal bowel gas pattern.

In the domain of infectious diseases, a predictive instrument for sepsis (i.e., overwhelming infection that would require certain emergency treatments) includes as key variables the patient's level of consciousness, specific complaints, and monitored physiologic measures such as blood pressure (especially low), heart rate (especially high), respiratory rate (especially high), body temperature (especially either unduly high or unduly low), ECG abnormalities (as not showing a contrary cardiac cause for derangements in heart rate, blood pressure, respiratory rate and other findings in the form of an interaction term in the mathematical model) laboratory tests such as white blood count (either unduly high or unduly low), interleukin levels, and other special blood tests typically available on-line from hospital clinical information systems. Also, other ongoing monitoring data relating to blood and other body fluid culture results, such as are typically available on electronic clinical information systems, are further important explanatory variables relating to the source of sepsis.

Each of the above diagnoses to be predicted have consequences in terms of clinical outcomes including, for example, mortality. Other outcomes that can be predicted by a predictive instrument include mortality due to acute myocardial infarction or congestive heart failure, as well as conditional outcomes such as are obtained from the thrombolytic predictive instrument (see U.S. Pat. No. 4,998,535). The use of this approach also applies to other noncardiac conditions for which prediction of medical outcomes can be conditioned on the use of specific therapies.

The examples presented above are meant to be merely illustrative of the many ways in which a predictive instrument can be used in continuously monitoring a patient's medical condition. It is not intended that the invention be limited to the few examples that were described here. In general, the predictive instrument is any instrument which computes on the basis of a set of clinical features a probability of a medical outcome or diagnosis. It is intended that the invention cover the use of such predictive instruments to continuously monitor any medical condition that lends itself to such monitoring, regardless of the particular set of clinical features and regardless of the particular medical outcome or diagnosis.

By clinical features, it should be understood that we mean any data form that gives direct information about the clinical, i.e., the medical, state of patient. Some of the variables used in the above descriptions have focused on circumstances in which clinical features can be directly acquired in electronic form, such as heart rate and respiratory rate acquired by monitors, such as waveforms acquired by an electrocardiograph, such as oxygen saturation measured by a sensor attached to the patient's finger, and such as biochemical laboratory results. However, other clinical features can be obtained in other forms and in other ways as well. For example, as described above in connection with the use of the cardiac predictive instrument, direct questioning of the patient provides important clinical features, namely, whether or not the patient is having chest pain and whether chest pains are the chief complaint. Analogously, for a predictive instrument for predicting various respiratory diagnoses or outcomes, a relevant clinical feature would be an indication as to whether the patient has shortness of breath. These symptoms are linked to the relevant underlying medical processes and can, in combination with other clinical variables in the mathematical model, add important information. And in the case of a predictive instrument for predicting neurologic problems, relevant clinical features include indications as to whether the patient has a headache and/or neurologic symptoms. In addition, some sources of data that are less directly connected to the patient but nevertheless still represent important clinical features. For example, sociodemographic data such as age and gender are obviously important, as was the case for the cardiac predictive instrument described above. In addition, other relevant clinical feature data is reflected in medical insurance claims, such as the mere performance of certain tests, the fact of hospitalization, the actual diagnostic code (e.g. the ICD9 Code), etc. A clinical feature is any piece of additional information about the patient, which when incorporated into a mathematical model predicts a given medical outcome.

A medical outcome or medical diagnosis, such as might be predicted by a predictive instrument, is defined in the following way. A medical outcome is the state of a patient defined in medical terms, typically described in the context of a particular constellation of presenting symptoms and clinical features. In practice, the outcome is selected to be clinically meaningful to the care of the patient. Therefore, an important medical outcome for a patient with a heart attack is mortality. For a person with respiratory failure, it is also mortality but it is also long-term respiratory disability, which might be defined, for example, as lack of ability to do activities of daily living due to shortness of breath as well. For a person with neurologic presenting symptoms, an important medical outcome is preservation of normal mental function as well as mortality.

There is overlap between the concept of medical outcomes and medical diagnoses. For example, when a decision has to be made about a patient, before the clinician can evaluate the likely ultimate outcome, the clinician must first consider the specific medical diagnosis or family of diagnoses that the patient has which require attention. Thus, a diagnosis is, in a sense, an intermediate "outcome". For a person coming to the emergency department with chest pain and/or other signs and symptoms, the first question on the clinician's mind is, what is the diagnosis? If the diagnosis, i.e., the ongoing medical/clinical process, is acute cardiac ischemia (i.e., occlusion of a coronary artery), then this requires treatment to prevent its potential downstream outcomes from occurring (e.g., death) and that treatment is very different from what would be used if the diagnosis is costocondritis (inflammation of the joints of the sternum), stomach ulcer, or some other cause of the symptoms. Moreover, for all the medical conditions alluded to above, detecting through continuous monitoring of the patient changes in the likelihood of such diagnoses can have very important clinical implications for treatment. That is, very different treatments are needed for acute cardiac ischemia as compared to an ulcer, for respiratory failure as compared to a cold, or for a rupture of a cerebral aneurism as compared to a tension headache. Thus, it can be critically important to detect when the probability of a medical outcome changes.

From the above, it should be apparent that the invention can be used with a wide variety of patient monitoring devices including, for example, heart rate monitors, respiratory rate monitors, bioanalyzers, blood oximeters, and fetal monitors, just to name a few.

What is claimed is:

1. An apparatus for continuously monitoring the medical condition of a patient, said apparatus comprising:

a medical instrument which during use monitors one or more clinical features of the patient;

a predictive instrument receiving output from the medical instrument, said predictive instrument programmed to complete a monitoring cycle in which it uses the output from the medical instrument to compute a probability of a medical outcome or diagnosis based on the monitored one or more clinical features; and a control module causing said predictive instrument to periodically repeat the monitoring cycle;

a detector module receiving the computed probabilities resulting from the repeated monitoring cycles and computing therefrom a change-of-condition measure, said detector module further configured to compare during each monitoring cycle the computed change-of-condition measure for that monitoring cycle to a threshold value and if in excess of said threshold value to generate an alarm notification.

2. The apparatus of claim 1 wherein said change-of-condition measure reflects a change in a computed probability for a current monitoring cycle as compared to a previous monitoring cycle.

3. The apparatus of claim 1 wherein the predictive instrument and the detector module are implemented remotely from each other.

4. A method for continuously monitoring the medical condition of a patient, said method comprising:

continuously monitoring one or more clinical features of the patient;

periodically computing a probability of a medical outcome or diagnosis based upon the continuously monitored one or more clinical features;

from the periodically computed probability of a medical outcome or diagnosis, computing a change-of-condition measure;

periodically comparing the change-in-condition measure to a threshold value; and if any computed change-in-condition measure exceeds said threshold value, generating an alarm notification.

5. The method of claim 4 wherein said change-of-condition measure represents a change in a computed probability for a current monitoring cycle relative to a previous monitoring cycle.

* * * * *